(12) United States Patent
Carmody et al.

(10) Patent No.: US 8,291,936 B2
(45) Date of Patent: Oct. 23, 2012

(54) NON-RETURN VALVE, IN PARTICULAR FOR MEDICAL USES

(75) Inventors: Colm Carmody, County Kerry (IE); Kieran Costello, Ballina/Killaloe County Clare (IE)

(73) Assignee: Illinois Tool Works Inc., Glenview, IL (US)

( * ) Notice: Subject to any disclaimer, the term of this patent is extended or adjusted under 35 U.S.C. 154(b) by 179 days.

(21) Appl. No.: 12/673,491

(22) PCT Filed: Jul. 24, 2008

(86) PCT No.: PCT/EP2008/006099
§ 371 (c)(1),
(2), (4) Date: Feb. 13, 2010

(87) PCT Pub. No.: WO2009/021605
PCT Pub. Date: Feb. 19, 2009

(65) Prior Publication Data
US 2011/0108147 A1    May 12, 2011

(30) Foreign Application Priority Data

Aug. 13, 2007  (DE) .................... 20 2007 011 322 U
Sep. 11, 2007  (DE) .................... 20 2007 012 680 U

(51) Int. Cl.
*F16K 15/14*    (2006.01)
(52) U.S. Cl. .................... 137/843; 137/859; 137/512.1
(58) Field of Classification Search ............ 137/512.15, 137/859, 512.1, 843
See application file for complete search history.

(56) References Cited

U.S. PATENT DOCUMENTS

| 4,141,379 A | 2/1979 | Manske |
| 7,673,653 B2 * | 3/2010 | Mijers et al. ................. 137/859 |
| 2007/0163664 A1 * | 7/2007 | Mijers et al. ................. 137/859 |

FOREIGN PATENT DOCUMENTS

| EP | 0031988 A1 | 7/1981 |
| EP | 1703183 A1 | 9/2006 |
| GB | 690897 A | 4/1953 |

OTHER PUBLICATIONS

ISR for PCT/EP2008/006099 dated Dec. 22, 2008.

* cited by examiner

*Primary Examiner* — Kevin Lee
*Assistant Examiner* — Macade Brown
(74) *Attorney, Agent, or Firm* — Lowe Hauptman Ham & Berner LLP

(57) ABSTRACT

A nonreturn valve includes a first tube connection housing and a second tube connection housing and a diaphragm disk between the first and second tube connection housings. The disk can be lifted from an annular valve seat upon an overpressure in an inlet channel and can be pressed onto the valve seat upon an overpressure in an outlet channel. The diaphragm disk has an annular bead received in mutually opposite annular grooves of the tube connection housings. The diaphragm disk is provided, radially outside the valve seat, with openings leading to an outlet chamber. The second tube connection housing lying opposite the openings is provided with recesses which communicate with the outlet channel and are separated from each other by supporting surfaces for the diaphragm disc. The recesses are connected to the outlet channel by narrow deep grooves.

10 Claims, 3 Drawing Sheets

NON-RETURN VALVE, IN PARTICULAR FOR MEDICAL USES

RELATED APPLICATIONS

The present application is national phase of PCT/EP2008/006099 filed Jul. 24, 2008, and claims priority from German Application Number 20 2007 011 322.6 filed Aug. 13, 2007 and German Application Number 20 2007 012 680.8 filed Sep. 11, 2007, the disclosures of which are hereby incorporated by reference herein in their entirety.

BACKGROUND

1. Technique Field

The invention relates to a nonreturn valve, in particular for medical uses.

2. Related Art

A nonreturn valve of this type, according to an earlier proposal by the applicant, is known from German utility model 20 2006 016 730.7.

These types of nonreturn valves for the medical field are required in infusion systems, diagnostic equipment, intravenous tube lines and the like, and therefore these types of nonreturn valves have to close in a very reliable manner and the closing time must be only fractions of seconds, in order thereby to avoid any backflow of liquids charged with undesired substances. Moreover, at the same time, production not only has to be extremely economical but also statistically very accurate, since valves of this kind can be used for medical applications exclusively as disposable articles and consequently, for cost reasons, have to be produced in very large numbers in an automated manner. At the same time, there are very strict legal regulations in respect of constant and uniform functional reliability, which is carefully monitored in Germany for example by the Technical Inspection Agency.

A valve of the abovementioned type is an improvement on a nonreturn valve according to another earlier proposal by the applicant, known from German utility model 20 2004 009 358.8, and thus ensures that, when there are high pressures on the inlet side of the valve, a situation can no longer arise where the openings provided in the diaphragm are able to bear on the opposite wall of the outlet chamber because of this overpressure and thus cause the valve to unintentionally close. This improvement is achieved by the numerous supporting surfaces between the recesses, which supporting surfaces ensure that, in the area of the openings in the diaphragm disk, a connection to the outlet chamber is maintained in any case, even if the diaphragm disk were to bear fully on the supporting surfaces.

SUMMARY

The object of the present invention is to further improve this valve of the type mentioned at the outset in terms of high pressures, and to completely eliminate damage or overstretching of the diaphragm disk.

In a nonreturn valve of the type mentioned at the outset, this object is achieved principally by the fact that the supporting surfaces and the grooves end at the center on a substantially plane support that protrudes in the direction of the diaphragm disk. This affords the advantage that, in the area of the diaphragm disk most sensitive to overstretching, the diaphragm disk is additionally supported centrally on the support in the event of high pressures, such that overstretching in the direction of the recesses between the supporting surfaces can be eliminated.

In a preferred embodiment according to the disclosure, a nonreturn valve is provided, in particular for medical uses, with a first tube connection housing and a second tube connection housing and, arranged between the two tube connection housings, a diaphragm disk which is made of flexible material and which, when there is an overpressure in an inlet channel of the first tube connection housing, can be lifted from an annular valve seat surrounding an inlet chamber connected to the inlet channel, and which, when there is an overpressure in an outlet channel of the second tube connection housing, can be pressed reliably and within minimal times onto the valve seat, wherein the diaphragm disk, at its outer peripheral area, is provided with an annular bead which is received in mutually opposite annular grooves of the tube connection housings, and the diaphragm disk is provided, radially outside the valve seat, with openings leading to an outlet chamber, and wherein the wall of the second tube connection housing lying opposite the openings is provided with recesses which communicate with the outlet channel, are separated from each other by supporting surfaces for the diaphragm disk and are connected to the outlet channel by narrow deep grooves.

In a preferred embodiment according to the invention, the support is designed with a circular shape. This creates particularly favorable conditions in terms of symmetry.

In a particularly preferred embodiment according to the invention, the diaphragm disk is provided with a protruding, integrally formed reinforcement. This ensures particularly reliable support of the diaphragm disk at high pressures, without the diaphragm disk undergoing excessive wear on the bearing surface on the support.

It is also preferable if small ribs are formed in the surface of the support and lead to the outer periphery of the latter. In this way, an additional connection carrying media is created over the cross section of the support.

It is preferable if the ribs are arranged intersecting one another in a star shape at the center of the support, in particular with three such ribs being especially preferred.

At high pressures, the diaphragm touches the support in the outlet of the nonreturn valve. After the pressure has been relieved, it can happen that the diaphragm stays sucked on the support and delays the closure of the valve. The ribs prevent this sucking and therefore contribute to the valve closing as quickly as possible.

The invention can be further refined specifically if the periphery of the support is arranged inside the radius of the opposite valve seat. This ensures particularly trouble-free operation of the valve.

BRIEF DESCRIPTION OF THE DRAWINGS

The invention is explained in more detail below on the basis of an embodiment depicted as an example in the drawings, in which.

DETAILED DESCRIPTION

Figure 1:
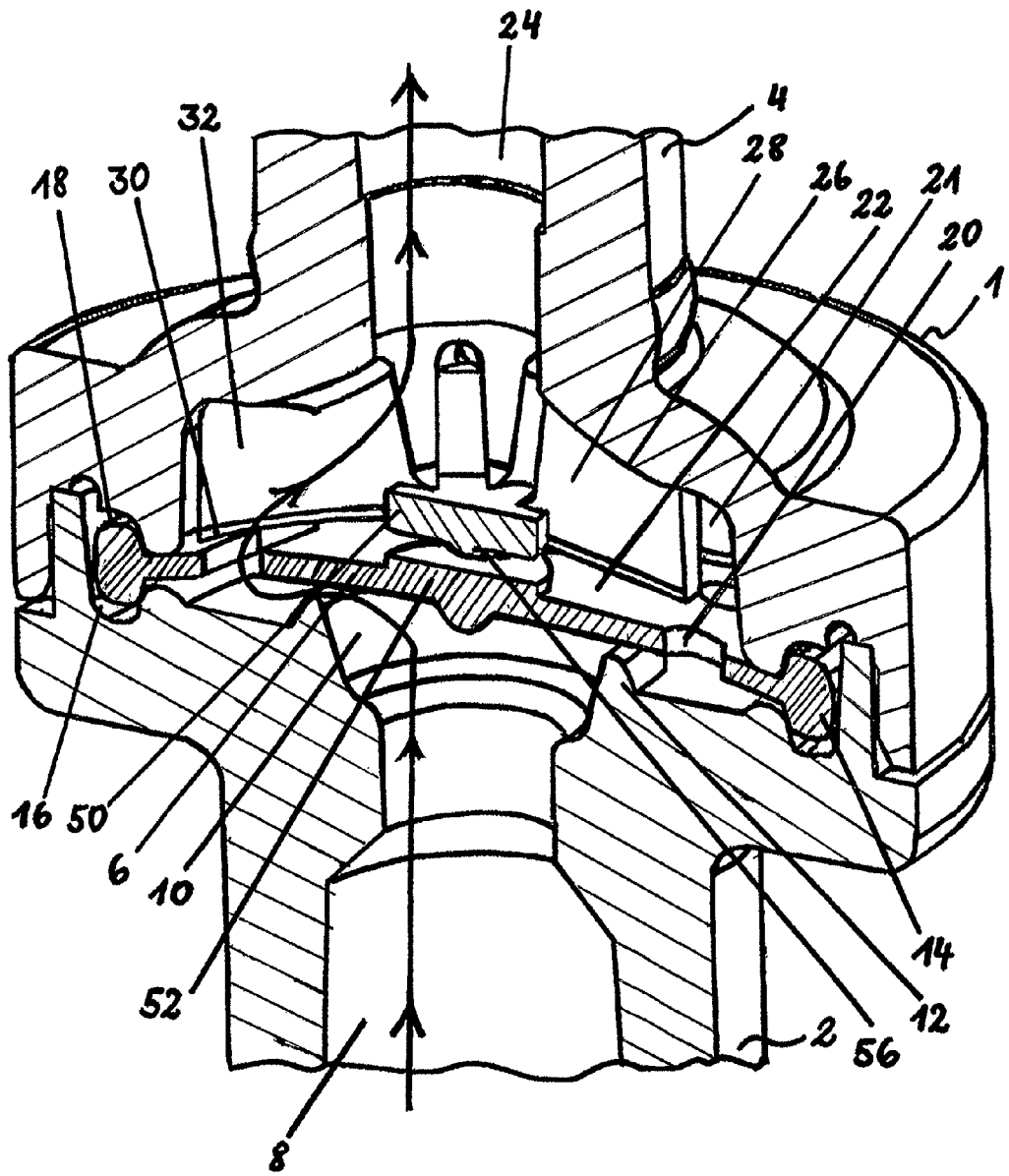
FIG. 1 shows a schematic sectional view, in the plane of the grooves, of an embodiment of the nonreturn valve according to the invention in the open state.

The nonreturn valve 1 shown greatly enlarged in the drawings is suitable in particular for the field of medicine and can be used, for example, at pressure differences of as low as 0.002 bar. The nonreturn valve 1 is composed of a first tube connection housing 2 and of a second tube connection housing 4, which are preferably produced from plastic by injection molding. A diaphragm disk 6 made from a flexible plastic, for example silicone, is arranged between the two tube connection housings 2 and 4.

In the first tube connection housing 2, an inlet channel 8 is formed which opens into an inlet chamber 10. The inlet chamber 10 is surrounded by an annular valve seat 12, against which the diaphragm disk 6 is pretensioned.

The diaphragm disk is designed with a continuously closed central part, which allows considerable tensile forces to be transmitted radially from the inside outward, and vice versa. At its outer peripheral area, the diaphragm disk 6 is provided with an integrally formed annular bead 14 which, for example, is produced by injection molding on the diaphragm disk 6. The first tube connection housing 2 contains, in its end face, an annular groove 16 which lies opposite an annular groove 18 in the second tube connection housing in the assembled state. When the two tube connection housings 2 and 4 are joined together, the annular bead 14 is received in the mutually opposite annular grooves 16 and 18 and at the same time is pretensioned against the valve seat 12.

Figure 2:
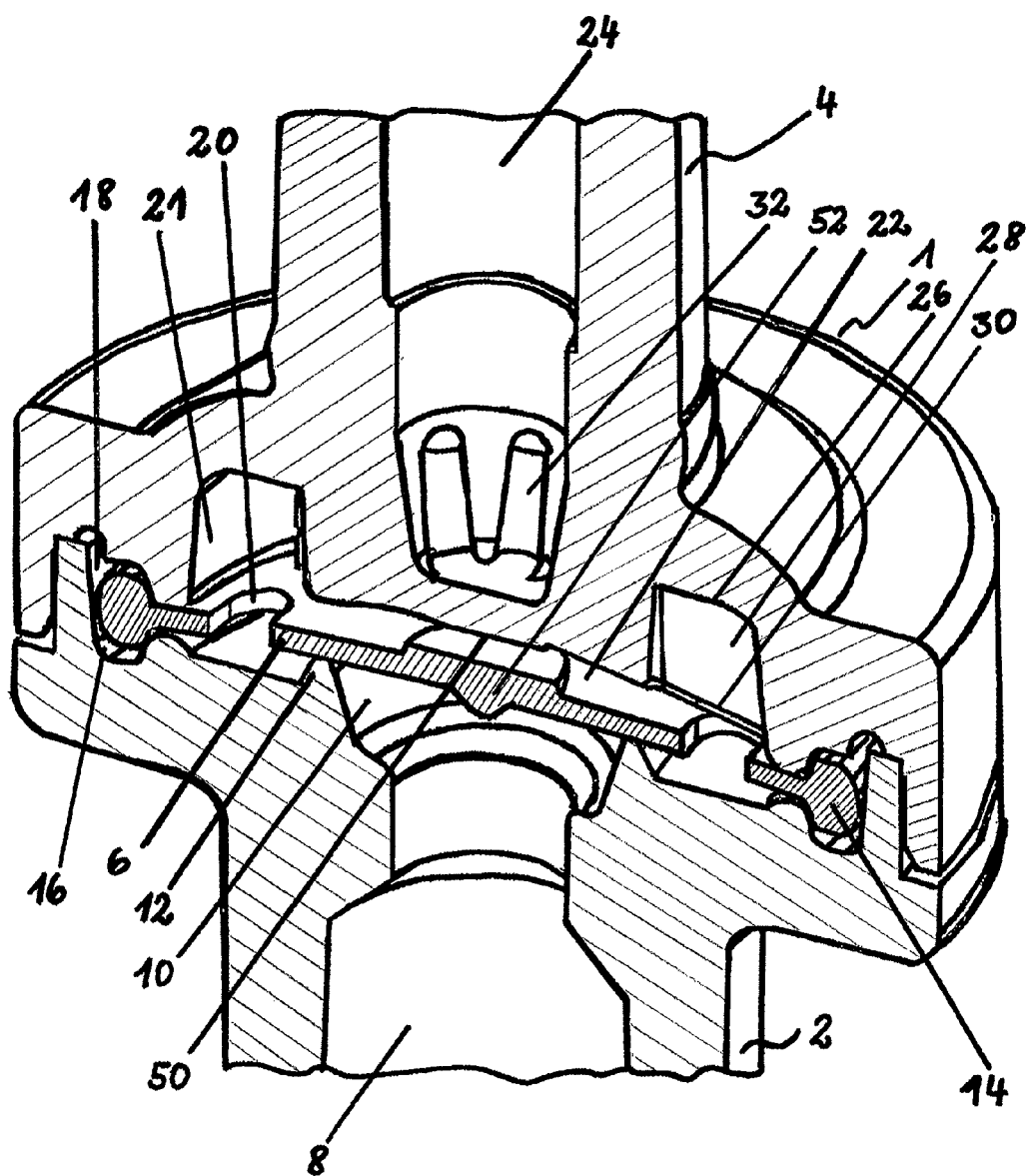
FIG. 2 shows a sectional view corresponding to FIG. 1, in the plane of the supporting surfaces of the valve according to FIG. 1, in the closed state.

As can be seen from FIGS. 1 and 2, the diaphragm disk 6 is provided, radially outside the valve seat 12, with openings 20 arranged on a radius that allows an annular chamber 21 lying radially outside the valve seat 12 in the first tube connection housing 2 to be connected to an outlet chamber 22 in the second tube connection housing 4, which outlet chamber 22 is in turn connected to the outlet channel 24 of the second tube connection housing 4.

Recesses, generally denoted by reference number 28, are provided in a wall of the outlet chamber 22 lying opposite the openings in the diaphragm disk, which recesses at the same time lie opposite the openings 20.

The recesses 28 are separated from one another by supporting surfaces 30 for the diaphragm disk 6, the recesses 28 being connected to the outlet channel 24 via narrow deep grooves 32.

The supporting surfaces 30, which widen in the direction of the outer edge of the outlet chamber 22 and reach as far as this outer edge, form the largest possible contact area for the diaphragm disk 6 at high pressures.

In the embodiment shown in the drawings, the supporting surfaces 30 and the grooves 32 end at the center on a support 50 which protrudes in the direction of the diaphragm disk 6 and which has a substantially flat surface. In the illustrative embodiment shown, the support 50 is designed with a circular shape, although other shapes are likewise possible.

The diaphragm disk 6 has a reinforcement 52 which, in the drawing, protrudes in the direction of the support 50, from the side lying opposite the support 50, but can also lie on the other side of the diaphragm disk 6. The protruding reinforcement 52 is likewise formed integrally with the diaphragm disk 6, for example by injection molding.

Figure 3:
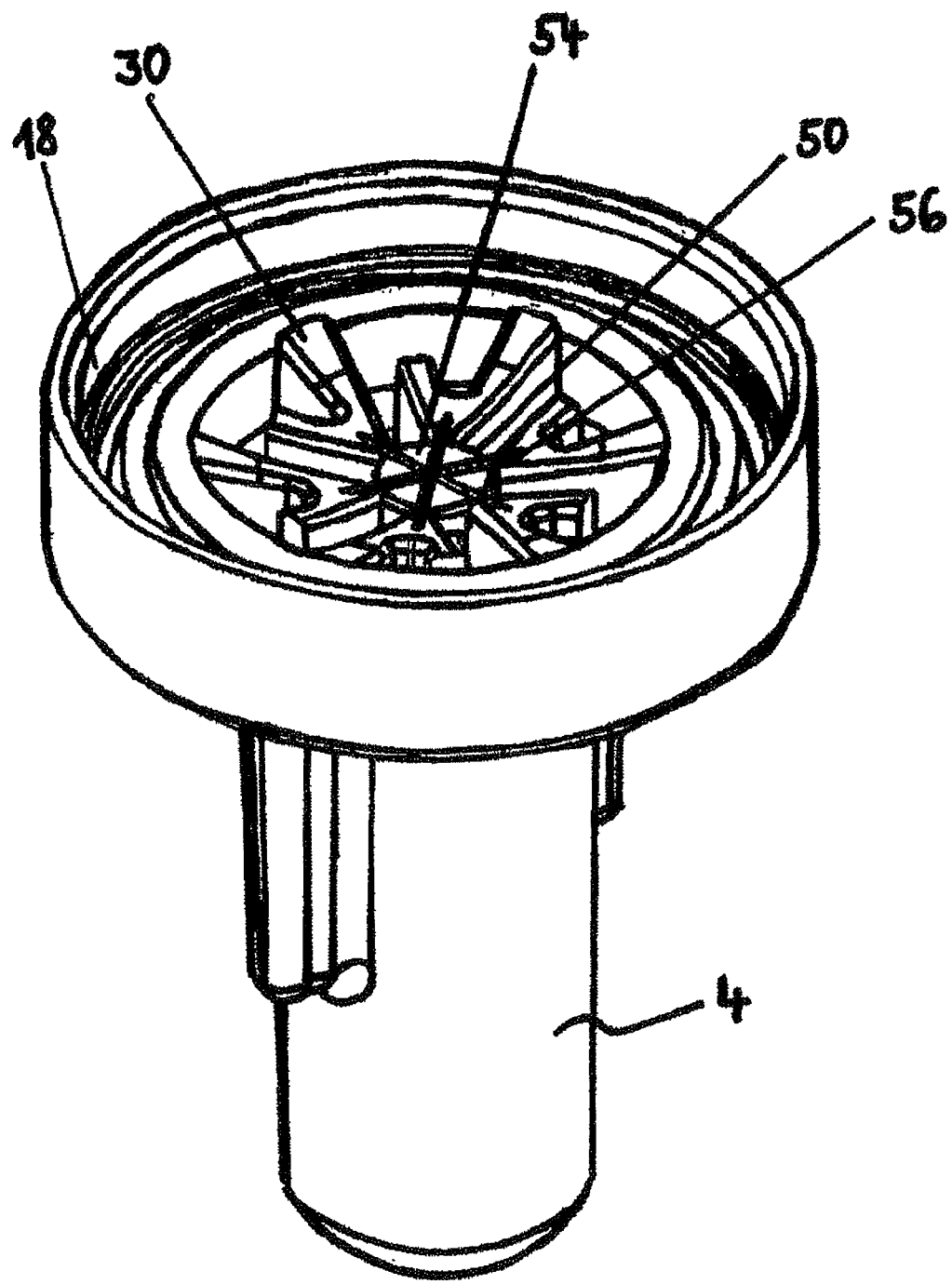
FIG. 3 shows a perspective view of the tube connection housing that contains the supporting surfaces and that forms the output side of the valve.

As can be seen from the view in FIG. 3, small ribs 56 are additionally formed on the surface 54 of the support 50, which small ribs 56 protrude beyond the surface 54 of the support 50 and lead to the outer periphery of the support 50. In the illustrative embodiment shown, the ribs 56 are continued into the supporting surfaces 30.

The ribs 56, of which there are three in the illustrative embodiment, intersect one another in a star shape at the center of the support 50. Moreover, the periphery of the support 50 lies inside the radius of the opposite valve seat 12.

If, in the embodiment shown, a substantial overpressure arises in the inlet channel 8 and causes the diaphragm disk 6 to be pressed against the wall 26 in an undesired manner, the reinforcement 52, or the rear face thereof if said reinforcement 52 lies under the diaphragm, first comes to bear on the support 50, such that the diaphragm disk 6 is additionally supported at the center. If the pressure continues to be too great, the diaphragm disk will then lay itself against the supporting surfaces 30, such that excessive stretching or deformation of the diaphragm disk does not occur.

Because of the hysteresis effect, diaphragms of this kind that are overstretched tend not to be able to quickly recover their original shape. The construction according to the present invention ensures that the diaphragm is supported and prevents the diaphragm from being overstretched at the relevant pressures. This feature therefore guarantees rapid closure of the valve when the pressure is relieved.

All the features and advantages of the invention set out in the description, claims and drawings, including structural details and spatial arrangements, can be essential to the invention both individually and also in any desired combination.

The invention claimed is:

1. A nonreturn valve, comprising:
a first tube connection housing having an inlet channel, an inlet chamber connected to the inlet channel and an annular valve seat surrounding the inlet chamber; and
a second tube connection housing coupled with the first tube connection housing, wherein said second tube connection housing includes
an outlet channel;
an outlet chamber connected to the outlet channel;
grooves; and
recesses fluidly connecting at least one of the grooves with the outlet channel;
a diaphragm disk between the two tube connection housings and made of flexible material, said diaphragm disk including
an annular protrusion arranged outside of the annular valve seat and configured to be received in mutually opposite annular grooves of the first and second tube connection housings; and
a plurality of openings arranged radially between the annular valve seat and the annular protrusion;
a plurality of supporting walls spaced circumferentially about the outlet channel in the second tube connection housing for supporting the diaphragm disk and arranged opposite to the openings, respectively;
a support directly connected with the supporting walls in the second tube connection housing and protruding toward the diaphragm disk; and
ribs disposed on a surface of the support and extending beyond an outer periphery of the support,
wherein
the disk is adapted to be lifted from the annular valve seat toward the second tube connection housing upon an overpressure in the inlet channel,
the disk is adapted to be pressed onto the valve seat upon an overpressure in the outlet channel, and
the supporting walls and the grooves radially extend toward a center of the support.

2. The nonreturn valve as claimed in claim 1, wherein the ribs intersect one another at the center of the support.

3. The nonreturn valve as claimed in claim 2, wherein the ribs extend outwardly into support surfaces of the supporting walls.

4. The nonreturn valve as claimed in claim 1, wherein each of the ribs extends in a direction defined by two opposite supporting walls and across the center of the support.

5. A nonreturn valve, comprising:
a first tube connection housing having an inlet channel, an inlet chamber connected to the inlet channel and an annular valve seat surrounding the inlet chamber; and
a second tube connection housing coupled with the first tube connection housing, wherein said second tube connection housing includes
an outlet channel;
an outlet chamber connected to the outlet channel;
grooves; and
recesses fluidly connecting at least one of the grooves with the outlet channel;
a diaphragm disk between the two tube connection housings and made of flexible material, said diaphragm disk including
an annular protrusion arranged outside of the annular valve seat and configured to be received in mutually opposite annular grooves of the first and second tube connection housings; and
a plurality of openings arranged radially between the annular valve seat and the annular protrusion;
a plurality of supporting walls spaced circumferentially about the outlet channel in the second tube connection housing for supporting the diaphragm disk and arranged opposite to the openings, respectively; and
a support directly connected with the supporting walls in the second tube connection housing and protruding toward the diaphragm disk,
wherein
the disk is adapted to be lifted from the annular valve seat toward the second tube connection housing upon an overpressure in the inlet channel,
the disk is adapted to be pressed onto the valve seat upon an overpressure in the outlet channel,
the supporting walls and the grooves radially extend toward a center of the support,
the diaphragm disk has a central protruding reinforcement, and
the center of the support overlaps the central protruding reinforcement of the diaphragm disk.

6. A nonreturn valve, comprising:
a first tube connection housing having an inlet channel, an inlet chamber connected to the inlet channel and an annular valve seat surrounding the inlet chamber; and
a second tube connection housing coupled with the first tube connection housing, wherein said second tube connection housing includes
an outlet channel;
an outlet chamber connected to the outlet channel;
grooves; and
recesses fluidly connecting at least one of the grooves with the outlet channel;
a diaphragm disk between the two tube connection housings and made of flexible material, said diaphragm disk including
an annular protrusion arranged outside of the annular valve seat and configured to be received in mutually opposite annular grooves of the first and second tube connection housings; and
a plurality of openings arranged radially between the annular valve seat and the annular protrusion;
a plurality of supporting walls spaced circumferentially about the outlet channel in the second tube connection housing for supporting the diaphragm disk and arranged opposite to the openings, respectively; and
a support directly connected with the supporting walls in the second tube connection housing and protruding toward the diaphragm disk,
wherein
the disk is adapted to be lifted from the annular valve seat toward the second tube connection housing upon an overpressure in the inlet channel,
the disk is adapted to be pressed onto the valve seat upon an overpressure in the outlet channel,
the supporting walls and the grooves radially extend toward a center of the support, and
the support has a substantially flat surface opposite to a surface from which the support protrudes toward the diaphragm disk.

7. A nonreturn valve, comprising:
a first tube connection housing having an inlet channel, an inlet chamber connected to the inlet channel and an annular valve seat surrounding the inlet chamber; and
a second tube connection housing coupled with the first tube connection housing, wherein said second tube connection housing includes
an outlet channel;
an outlet chamber connected to the outlet channel;
grooves; and
recesses fluidly connecting at least one of the grooves with the outlet channel;
a diaphragm disk between the two tube connection housings and made of flexible material, said diaphragm disk including
an annular protrusion arranged outside of the annular valve seat and configured to be received in mutually opposite annular grooves of the first and second tube connection housings; and
a plurality of openings arranged radially between the annular valve seat and the annular protrusion;
a plurality of supporting walls spaced circumferentially about the outlet channel in the second tube connection housing for supporting the diaphragm disk and arranged opposite to the openings, respectively; and
a support directly connected with the supporting walls in the second tube connection housing and protruding toward the diaphragm disk,
wherein
the disk is adapted to be lifted from the annular valve seat toward the second tube connection housing upon an overpressure in the inlet channel,
the disk is adapted to be pressed onto the valve seat upon an overpressure in the outlet channel,
the supporting walls and the grooves radially extend toward a center of the support, and
the support is directly connected with each of the supporting walls at the center of the support.

8. The nonreturn valve as claimed in claim 7, wherein the support has a circular shape.

9. The nonreturn valve as claimed in claim 7, wherein the diaphragm disk has a central protruding reinforcement.

10. The nonreturn valve as claimed in claim 7, wherein the support extends outwardly toward an outer periphery of the second tube connection housing without extending beyond the annular valve seat.

* * * * *